United States Patent
Surti et al.

(10) Patent No.: US 12,419,496 B2
(45) Date of Patent: *Sep. 23, 2025

(54) FLEXIBLE ENDOSCOPIC SUPPORT SYSTEM

(71) Applicant: Cook Medical Technologies LLC, Bloomington, IN (US)

(72) Inventors: Vihar C. Surti, Winston-Salem, NC (US); John C. Sigmon, Jr., Winston-Salem, NC (US); William S. Gibbons, Jr., Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/759,175

(22) Filed: Jun. 28, 2024

(65) Prior Publication Data

US 2024/0349990 A1 Oct. 24, 2024

Related U.S. Application Data

(60) Continuation of application No. 17/401,085, filed on Aug. 12, 2021, now Pat. No. 12,053,154, which is a
(Continued)

(51) Int. Cl.
*A61B 1/00* (2006.01)
*A61B 1/005* (2006.01)
(Continued)

(52) U.S. Cl.
CPC ...... *A61B 1/00098* (2013.01); *A61B 1/00114* (2013.01); *A61B 1/00128* (2013.01);
(Continued)

(58) Field of Classification Search
CPC ............ A61B 1/00098; A61B 1/00114; A61B 1/00128; A61B 1/00133; A61B 1/00137;
(Continued)

(56) References Cited

U.S. PATENT DOCUMENTS

| 3,557,780 A | 1/1971 | Sato |
| 3,896,793 A | 7/1975 | Mitsui et al. |

(Continued)

FOREIGN PATENT DOCUMENTS

| CN | 105078398 A | 11/2015 |
| EP | 2 596 741 A1 | 5/2013 |

(Continued)

OTHER PUBLICATIONS

PCT Notice of Transmittal of International Search Report in related application No. PCT/US2017/019850, dated Jul. 17, 2017, 5 pages.
(Continued)

*Primary Examiner* — Timothy J Neal
(74) *Attorney, Agent, or Firm* — Vivacqua Crane, PLLC

(57) ABSTRACT

A scope system is provided including an elongate tube with a distal portion and a lumen extending therethrough. The scope system also includes at least one accessory channel including a tubular structure with an accessory lumen extending therethrough, the at least one accessory channel movably disposed at least partially within the lumen of the elongate tube. The at least one accessory channel includes a distal section and a forward-viewing configuration and a side-viewing configuration. In the forward-viewing configuration, the distal section of the at least one accessory channel is substantially parallel to the distal portion of the elongate tube and in the side-viewing configuration, the distal section of the at least one accessory channel is arced at a radius greater than a radius of the distal portion of the elongate tube.

20 Claims, 14 Drawing Sheets

Related U.S. Application Data continuation of application No. 16/749,083, filed on Jan. 22, 2020, now Pat. No. 11,122,962, which is a division of application No. 15/445,318, filed on Feb. 28, 2017, now Pat. No. 10,582,835.

(60) Provisional application No. 62/301,705, filed on Mar. 1, 2016.

(51) Int. Cl.
*A61B 1/008* (2006.01)
*A61B 1/018* (2006.01)
*A61B 1/05* (2006.01)
*A61B 1/06* (2006.01)
*A61B 1/273* (2006.01)

(52) U.S. Cl.
CPC ...... *A61B 1/00133* (2013.01); *A61B 1/00137* (2013.01); *A61B 1/00174* (2013.01); *A61B 1/0055* (2013.01); *A61B 1/008* (2013.01); *A61B 1/018* (2013.01); *A61B 1/05* (2013.01); *A61B 1/0623* (2013.01); *A61B 1/0684* (2013.01); *A61B 1/273* (2013.01)

(58) Field of Classification Search
CPC ......... A61B 1/0055; A61B 1/018; A61B 1/05; A61B 1/0684; A61B 1/00174; A61B 1/008; A61B 1/0623; A61B 1/273
See application file for complete search history.

(56) References Cited

U.S. PATENT DOCUMENTS

| | | | |
|---|---|---|---|
| 4,763,662 A * | 8/1988 | Yokoi | A61B 1/00098 600/101 |
| 5,005,558 A | 4/1991 | Aomori | |
| 5,143,475 A | 9/1992 | Chikama | |
| 5,749,828 A | 5/1998 | Solomon et al. | |
| 5,873,817 A | 2/1999 | Kokish et al. | |
| 6,071,279 A | 6/2000 | Whayne et al. | |
| 6,817,974 B2 | 11/2004 | Cooper et al. | |
| 8,771,171 B2 | 7/2014 | Onuki et al. | |
| 9,408,529 B2 | 8/2016 | Smith et al. | |
| 9,565,994 B2 | 2/2017 | Kappel et al. | |
| 9,986,996 B2 | 6/2018 | Hiernaux et al. | |
| 10,029,073 B2 | 7/2018 | Kabe et al. | |
| 10,076,236 B2 | 9/2018 | Ikeda et al. | |
| 10,321,804 B2 | 6/2019 | Jacobsen et al. | |
| 10,363,398 B2 | 7/2019 | Gerrans et al. | |
| 11,122,962 B2 | 9/2021 | Surti | |
| 11,503,984 B2 | 11/2022 | Surti et al. | |
| 12,053,154 B2 * | 8/2024 | Surti | A61B 1/008 |
| 2004/0138529 A1 * | 7/2004 | Wiltshire | A61B 1/0055 600/144 |
| 2004/0249367 A1 | 12/2004 | Saadat et al. | |
| 2005/0234297 A1 | 10/2005 | Devierre et al. | |
| 2006/0178560 A1 | 8/2006 | Saadat et al. | |
| 2006/0189845 A1 | 8/2006 | Maahs et al. | |
| 2008/0097293 A1 | 4/2008 | Chin | |
| 2008/0287961 A1 | 11/2008 | Miyamoto et al. | |
| 2008/0300462 A1 | 12/2008 | Intoccia et al. | |
| 2009/0171159 A1 | 7/2009 | Jorgenson | |
| 2010/0036198 A1 | 2/2010 | Tacchino et al. | |
| 2010/0298642 A1 | 11/2010 | Trusty | |
| 2012/0041264 A1 | 2/2012 | Blase | |
| 2012/0170970 A1 | 7/2012 | Kitagawa et al. | |
| 2012/0238805 A1 | 9/2012 | Iwasaka | |
| 2013/0041214 A1 | 2/2013 | Maahs | |
| 2013/0184528 A1 | 7/2013 | Onuki | |
| 2013/0231534 A1 | 9/2013 | Piskun | |
| 2014/0142393 A1 | 5/2014 | Piskun | |
| 2015/0032117 A1 | 1/2015 | Kim et al. | |
| 2015/0101442 A1 | 4/2015 | Romo | |
| 2016/0235400 A1 | 8/2016 | Hiernaux | |
| 2016/0288337 A1 | 10/2016 | Zubiate et al. | |
| 2017/0095645 A1 | 4/2017 | Toth | |
| 2017/0354318 A1 | 12/2017 | Rogers et al. | |
| 2018/0168432 A1 | 6/2018 | Banik et al. | |
| 2018/0360435 A1 | 12/2018 | Romo | |
| 2019/0104932 A1 | 4/2019 | Ostrovsky et al. | |
| 2019/0142413 A1 | 5/2019 | Fairneny | |

FOREIGN PATENT DOCUMENTS

| | | |
|---|---|---|
| GB | 2478988 A | 9/2011 |
| JP | S61-280849 A | 12/1986 |
| JP | S62-74348 A | 4/1987 |
| JP | S62-292135 A | 12/1987 |
| JP | S63-155116 A | 6/1988 |
| JP | H01-138522 A | 5/1989 |
| JP | H-07-327916 | 12/1995 |
| JP | H10-295635 A | 11/1998 |
| JP | 2003-204926 A | 7/2003 |
| JP | 2005-152452 A | 6/2005 |
| JP | 2007-532262 A | 11/2007 |
| JP | 2008-536552 A | 9/2008 |
| JP | 2009-018044 A | 1/2009 |
| JP | 2009-529390 A | 8/2009 |
| JP | 2010-063772 A | 3/2010 |
| JP | 2010-284503 A | 12/2010 |
| JP | 2011-062362 A | 3/2011 |
| JP | 2011-072413 A | 4/2011 |
| JP | 2013-066638 A | 4/2013 |
| JP | 2014-102390 A | 6/2014 |
| JP | 2015-512661 A | 4/2015 |
| JP | 2016-513500 A | 5/2016 |
| KR | 10-2012-0111603 | 10/2012 |
| WO | WO 2007/063904 A1 | 5/2009 |
| WO | WO 2012/111761 | 8/2012 |
| WO | 2015159619 A1 | 10/2015 |

OTHER PUBLICATIONS

PCT Written Opinion of the International Searching Authority in related application No. PCT/US2017/019850, 8 pages.
First Office Action from corresponding Japanese Application No. 2018-545873, dated Jul. 2, 2019, 4 pages, in Japanese language.
First Office Action from corresponding Chinese Application No. CN 2017800201892, dated Mar. 2, 2020, 11 pages, in Chinese language.
First Office Action from corresponding Chinese Application No. CN 2017800201892, dated Mar. 2, 2020, 7 pages, English translation.
Search Report from corresponding Chinese Application No. CN 2017800201892, dated Feb. 20, 2020, 2 pages, in Chinese language.
Second Office Action from corresponding Japanese Application No. JP 2018-545873, dated Feb. 25, 2020, 4 pages, in Japanese language.
Second Office Action from corresponding Japanese Application No. JP 2018-545873, dated Feb. 25, 2020, 4 pages, English translation.
First Office Action from corresponding Korean Application No. 10-2018-7027789, dated Feb. 19, 2020, 11 pages, in Korean language.
First Office Action from corresponding Korean Application No. 10-2018-7027789, dated Feb. 19, 2020, 10 pages, English translation.
Second Office Action from corresponding Chinese Application No. CN 201780020189.2, dated Jul. 1, 2021, 6 pages, in Chinese language.
First Office Action from corresponding Korean Application No. 10-2018-7027795, dated Apr. 2, 2020, 7 pages, in Korean language.
First Office Action from corresponding Korean Application No. 10-2018-7027795, dated Apr. 2, 2020, 6 pages, English translation.
Second Office Action from corresponding Japanese Application No. JP 2018-545842, dated Mar. 3, 2020, 4 pages, in Japanese language.
Second Office Action from corresponding Japanese Application No. JP 2018-545842, dated Mar. 3, 2020, 5 pages, English translation.
First Office Action from corresponding Chinese Application No. 2017800197045, dated Feb. 6, 2020, 5 pages, in Chinese language.
First Office Action from corresponding Chinese Application No. 2017800197045, dated Feb. 6, 2020, 5 pages, English translation.

(56) References Cited

OTHER PUBLICATIONS

Chinese Supplementary Search, dated Dec. 25, 2021, 1 page, Chinese Application No. CN 201780020189.2, State Intellectual Property Office of P.R. China, in Chinese language.
Chinese Supplementary Search, dated Jun. 27, 2021, pp. 1-2, Chinese Application No. CN 201780020189.2, State Intellectual Property Office of P.R. China, in Chinese language.
Chinese Supplementary Search, dated Sep. 27, 2020, pp. 1-2, Chinese Application No. CN 201780020189.2, State Intellectual Property Office of P.R. China, in Chinese language.
Third Chinese Office Action, dated Jul. 1, 2021, pp. 1-6, Chinese Application No. CN 201780020189.2, State Intellectual Property Office of P.R. China, in Chinese language.
Third Chinese Office Action, dated Jul. 1, 2021, pp. 1-8, Chinese Application No. CN 201780020189.2, State Intellectual Property Office of P.R. China, in English language.
Second Chinese Office Action, dated Oct. 10, 2020, pp. 1-10, Chinese Application No. CN 201780020189.2, State Intellectual Property Office of P.R. China, in Chinese language.
Second Chinese Office Action, dated Oct. 10, 2020, pp. 1-12, Chinese Application No. CN 201780020189.2, State Intellectual Property Office of P.R. China, in English language.
First Chinese Search, dated Jan. 21, 2020, 1 page, Chinese Application No. CN 201780019704.5, State Intellectual Property Office of P.R. China, in Chinese language.
Supplementary Chinese Search, dated Aug. 27, 2020, 1 page, Chinese Application No. CN 201780019704.5, State Intellectual Property Office of P.R. China, in Chinese language.
Japanese Search Report, dated Jun. 24, 2019, pp. 1-12, Japanese Application No. JP 2018-545873, Japanese Patent Office, in English language.
Japanese Search Report, dated Jun. 24, 2019, pp. 1-9 pages, Japanese Application No. JP 2018-545873, Japanese Patent Office, in Japanese language.
First Japanese Office Action, dated Sep. 24, 2019, pp. 1-5, Japanese Application No. JP 2018-545842, Japanese Patent Office, in English language.
First Japanese Office Action, dated Sep. 24, 2019, pp. 1-5, Japanese Application No. JP 2018-545842, Japanese Patent Office, in Japanese language.
Japanese Search Report, dated Aug. 29, 2019, pp. 1-17, Japanese Application No. JP 2018-545842, Japanese Patent Office, in English language.
Japanese Search Report, dated Aug. 29, 2019, pp. 1-17, Japanese Application No. JP 2018-545842, Japanese Patent Office, in Japanese language.
Third Japanese Office Action, dated Sep. 23, 2020, pp. 1-3, Japanese Application No. JP 2018-545842, Japanese Patent Office, in English language.
Third Japanese Office Action, dated Sep. 23, 2020, pp. 1-3, Japanese Application No. JP 2018-545842, Japanese Patent Office, in Japanese language.
First Japanese Office Action, dated Oct. 26, 2021, pp. 1-3, Japanese Application No. JP 2020-195283, Japanese Patent Office, in English language.
First Japanese Office Action, dated Oct. 26, 2021, pp. 1-3, Japanese Application No. JP 2020-195283, Japanese Patent Office, in Japanese language.
Japanese Search Report, dated Oct. 19, 2021, pp. 1-27, Japanese Application No. JP 2020-195283, Japanese Patent Office, in English language.
Japanese Search Report, dated Oct. 19, 2021, pp. 1-22, Japanese Application No. JP 2020-195283, Japanese Patent Office, Japanese language.
First Korean Office Action, dated Apr. 17, 2021, pp. 1-8, Korean Application No. KR 10-2021-7004020, Korean Intellectual Property Office, in English language.
First Korean Office Action, dated Apr. 17, 2021, pp. 1-6, Korean Application No. KR 10-2021-7004020, Korean Intellectual Property Office, in Korean language.
PCT International Search Report, dated Jul. 20, 2017, pp. 1-4, in PCT Application No. PCT/US2017/019851, European Patent Office, Rijswijk.
PCT Written Opinion of the International Searching Authority, dated Jul. 20, 2017, pp. 1-6, PCT Application No. PCT/US2017/019851, European Patent Office, Rijswijk.
European Office Action, dated Oct. 26, 2021, pp. 1-5, European Application No. EP17711411.3, European Office Action, Munich, German.
First Australian Office Action, dated Dec. 10, 2018, pp. 1-3, Australian Application No. AU2017227539, IP Australia.
First Australian Office Action, dated Dec. 10, 2018, pp. 1-5, Australian Application No. AU2017227540, IP Australia.
First Australian Office Action, dated Jun. 19, 2020, pp. 1-4, Australian Application No. AU2019268170, IP Australia.
Second Australian Office Action, dated May 20, 2021, pp. 1-3 pages, Australian Application No. AU2019268170, IP Australia.
First Japanese Office Action, dated Mar. 8, 2022, pp. 1-4, Japanese Application No. JP 2021-007913, Japanese Patent Office, in English language.
First Japanese Office Action, dated Mar. 8, 2022, pp. 1-3, Japanese Application No. JP 2021-007913, Japanese Patent Office, in Japanese language.
Second Office Action from Corresponding Japanese Application No. JP 2021-007913, dated Oct. 4, 2022, 2 pages, in Japanese language.
Second Office Action from Corresponding Japanese Application No. JP 2021-007913, dated Oct. 4, 2022, 3 pages, in English language.
Japanese Office Action with English translation, dated Jul. 19, 2023, pp. 1-10, issued in Japanese Patent Application No. 2022-098796, Japanese Patent Office, Tokyo. Japan.
European Patent Office. Article 94(3) Communication for EP Application No. 17711411.3, mailed Nov. 25, 2024, pp. 1-4.
Japan Patent Office. Non-Final Office Action for JP Application No. 2024-051052 and English translation, mailed May 7, 2025, pp. 1-8.

* cited by examiner

FLEXIBLE ENDOSCOPIC SUPPORT SYSTEM

CROSS-REFERENCE TO RELATED APPLICATIONS

This application is a continuation of U.S. patent application Ser. No. 17/401,085, filed Aug. 12, 2021, which is a continuation of U.S. patent application Ser. No. 16/749,083, filed Jan. 22, 2020 (and issued as U.S. Pat. No. 11,122,962), which was a divisional application of U.S. patent application Ser. No. 15/445,318, filed Feb. 28, 2017 (and issued as U.S. Pat. No. 10,582,835), which claimed the benefit of the filing date under 35 U.S.C. § 119 (e) of Provisional U.S. Patent Application Ser. No. 62/301,705 filed Mar. 1, 2016, each of which is hereby incorporated by reference.

FIELD

The present disclosure relates to medical devices and more specifically to endoscope systems.

BACKGROUND

The statements in this section merely provide background information related to the present disclosure and may not constitute prior art.

The duodenoscope is a medical device used in a variety of endoscopic procedures, including endoscopic retrograde cholangio-pancreatography (ERCP). In an ERCP, a physician inserts the duodenoscope into a patient's mouth, through the patient's gastrointestinal (GI) tract, and into the duodenum until the distal end of the duodenoscope is positioned near the papilla of Vater, a small mound-like structure that acts as the entrance from the common bile duct and pancreatic duct into the duodenum. The physician then uses a variety of tools and accessories that are passed through a lumen in the duodenoscope to access the common bile duct or pancreatic duct through the papilla of Vater.

However, the duodenoscope suffers from several design issues. For example, due to the location of the papilla of Vater and shape of the duodenoscope, the endoscope tools or accessories must be bent sharply at (or sometimes more than) 90 degree angles at the distal end of the duodenoscope, which results in significant friction between the tools and duodenoscope and accompanying force transmission loss. Therefore, the accessories must be durable enough to withstand this sharp bend and the physician must apply a greater force to continue to advance the tools than is desired. Further, the built-in camera system of the duodenoscope is side-facing, making it difficult for novices and even experienced physicians to navigate the duodenoscope through the GI tract. Also, traditional duodenoscopes only have one accessory channel, making the use of multiple accessories time intensive and cumbersome. Additionally, duodenoscopes are difficult to clean, which may result in inadequate cleaning of the device after use and potential bacterial contamination of patients during subsequent use of the duodenoscope.

Therefore, it is desirable to have an endoscope system that eliminates or lessens the force transmission losses of traditional duodenoscopes. Further, increased and easier maneuverability of an endoscope system through and within the GI tract is desired. It is also desirable to provide an endoscope system that is easy to clean or is disposable.

SUMMARY

In one form of the present disclosure, a scope system is provided. The scope system comprises an elongate tube comprising a lumen extending therethrough, the elongate tube further comprising a distal portion. The scope system also comprises at least one accessory channel comprising a tubular structure comprising an accessory lumen extending therethrough, the at least one accessory channel movably disposed at least partially within the lumen of the elongate tube, the at least one accessory channel comprising a distal section, the at least one accessory channel further comprising a forward-viewing configuration and a side-viewing configuration. Additionally, in the forward-viewing configuration, the distal section of the at least one accessory channel is substantially parallel to the distal portion of the elongate tube, and in the side-viewing configuration, the distal section of the at least one accessory channel is arced at a radius different (e.g., greater relative to a common centerpoint) than a radius of the distal portion of the elongate tube.

The at least one accessory channel of the scope system may also be movable in a distal direction which moves the at least one accessory channel from the forward-viewing configuration to the side-viewing configuration and the at least one accessory channel may be movable in a proximal direction which moves the at least one accessory channel from the side-viewing configuration to the forward-viewing configuration. The scope system may further include the distal portion comprising a pivot point, wherein during movement of the at least one accessory channel between the forward-viewing configuration and the side-viewing configuration, the at least one accessory channel rotates about the pivot point. The scope system may also comprise an axially rotatable bearing disposed between the distal portion of the elongate tube and a proximal portion, the axially rotatable bearing permitting rotation of the distal portion with respect to the proximal portion. The scope system may also further comprise first and second drive members connected to the distal portion of the elongate tube and extending proximally along the elongate tube, wherein proximal movement of the first drive member bends the distal portion of the elongate tube in a first direction, and proximal movement of the second drive member bends the distal portion of the elongate tube in a second direction. The system may further comprise a light connected to the distal portion, wherein one of the first and second drive members further comprises an electrical wiring between the light and a power source.

In another form of the present disclosure, a scope cap is provided. The scope cap comprises a housing comprising an attachment portion, the attachment portion configured to engage with a scope, the housing further comprising a pivot point. The scope cap also comprises at least one accessory channel engaged with the housing, the at least one accessory channel comprising a tubular structure comprising an accessory lumen extending therethrough, the at least one accessory channel further comprising a distal section and a proximal section, wherein the proximal section is configured to removably engage with the scope. Further, the distal section of the at least one accessory channel is rotatable about the pivot point to move the at least one accessory channel between a side-viewing configuration and a forward-viewing configuration.

The at least one accessory channel of the scope cap may also be rotated at least 45 degrees in the side-viewing configuration with respect to the distal section of the at least one accessory channel when in the forward-viewing configuration. Additionally, movement of the at least one accessory channel in a proximal direction may move the at least one accessory channel from the forward-viewing configuration to the side-viewing configuration, and movement of the at least one accessory channel in a distal direction may move the at least one accessory channel from side-viewing configuration to the forward-viewing configuration.

In yet another form of the present disclosure, a method is provided. The method comprises inserting the scope system into a patient's body, the scope system comprising an elongate tube comprising a lumen extending therethrough and at least one accessory channel movably disposed at least partially within the lumen of the elongate tube, the at least one accessory channel comprising a tubular structure comprising an accessory lumen extending therethrough. The method further comprises positioning the scope system in a forward-viewing configuration, wherein in the forward-viewing configuration a distal section of the at least one accessory channel is substantially parallel to a distal portion of the elongate tube. Also, the method comprises moving the scope system to a side-viewing configuration, wherein in the side-viewing configuration, the distal section of the at least one accessory channel is arced at a radius different than a radius of the distal portion of the elongate tube (i.e., greater relative to a common centerpoint, as shown in the drawings).

Further areas of applicability will become apparent from the description provided herein. It should be understood that the description and specific examples are intended for purposes of illustration only and are not intended to limit the scope of the present disclosure.

DRAWINGS

The drawings described herein are for illustration purposes only and are not intended to limit the scope of the present disclosure in any way.

DETAILED DESCRIPTION

Figure 1:
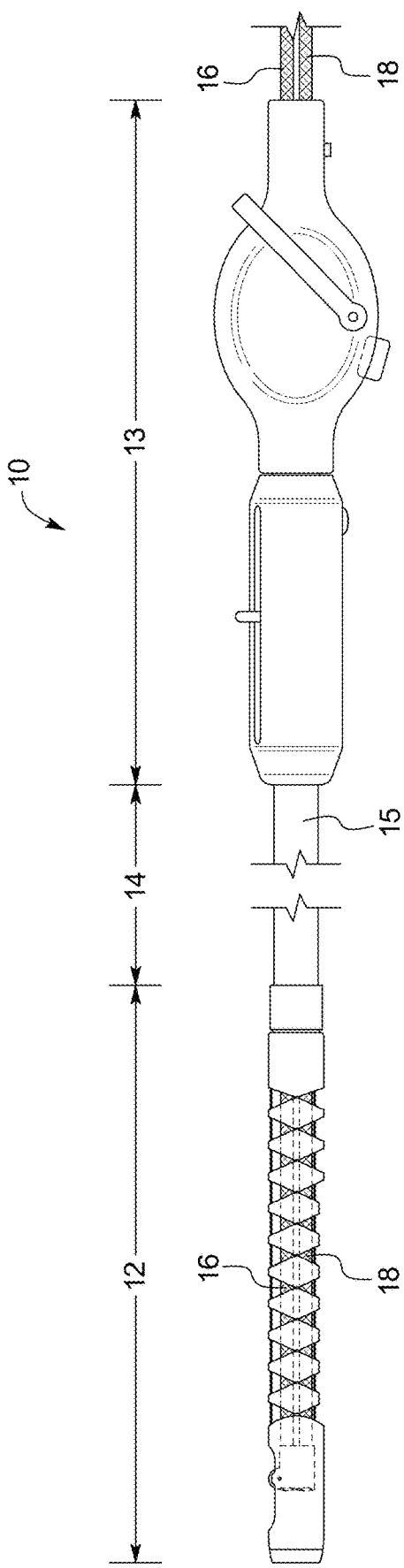
FIG. 1 is a drawing of an endoscope system.

The following description is merely exemplary in nature and is not intended to limit the present disclosure, application, or uses. It should be understood that throughout the drawings, corresponding reference numerals indicate like or corresponding parts and features. It should also be understood that various cross-hatching patterns used in the drawings are not intended to limit the specific materials that may be employed with the present disclosure. The cross-hatching patterns are merely exemplary of preferable materials or are used to distinguish between adjacent or mating components illustrated within the drawings for purposes of clarity.

Referring to FIG. 1, an endoscope system 10 is provided. The endoscope system 10 may be generally shaped as an elongate tube including a distal portion 12, a central portion 14, and a proximal, or handle, portion 13. The central portion 14 may be a flexible, elongate tube with at least one lumen 15 running throughout the length of the central portion 14. The central portion 14 may connect the distal portion 12 and proximal portion 13 together. The lumen 15 of the central portion 14 may extend through the distal 12 and handle portions 13 of the endoscope system 10 as well. The central portion 14 may be made of a braided material such as pebax with a polytetrafluoroethylene liner to provide sufficient torquability and pushability. Other potential materials for the central portion 14 include but are not limited to polyethylene, polypropylene, and nylon. The endoscope system 10 may further include two accessory channels 16, 18 each with lumens 17, 19 running therethrough (shown in FIG. 7). The accessory channels 16, 18 may be designed as individual elongated tubes that may be movable within the lumen 15 of the system 10, thus allowing longitudinal movement of the accessory channels 16, 18 with respect to the central portion 14. While this embodiment includes two accessory channels 16, 18, one or even three or more accessory channels may be used. For example, a single, larger accessory channel may be used to accommodate larger endoscopic tools. Further, in lieu of individual accessory channels 16, 18, a single elongate tube may be used with two or more lumens running through it. The accessory channels 16, 18 may range in diameter anywhere from 1 to 10 millimeters. In one exemplary embodiment, the first accessory channel 16 may be 4.2 millimeters in diameter while the second accessory channel 18 may be 3.7 millimeters in diameter. The accessory channels 16, 18 may extend proximally from or past the handle portion 13, through the lumen 15 and into the distal portion 12. Various tools, devices, and cameras may be inserted into and removed from the accessory channels 16, 18.

Figure 2:
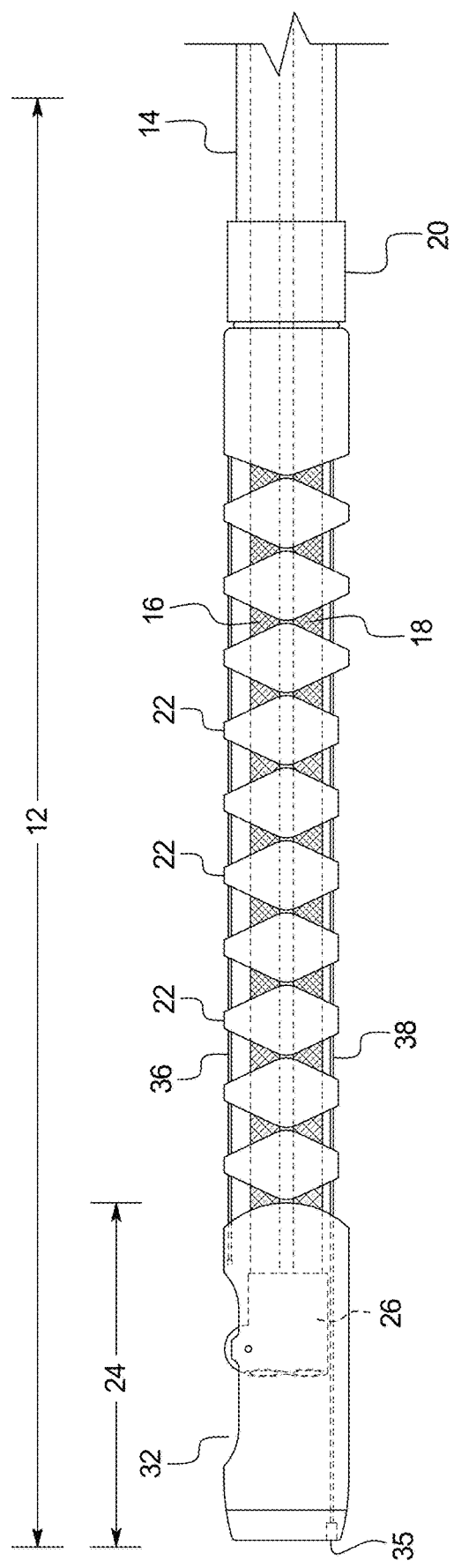
FIG. 2 is a detailed view of the distal portion of an endoscope system in a forward-facing configuration.

Now referring to FIG. 2, a detailed view of the distal portion 12 of the endoscope system 10 is shown. The endoscope system 10 may include a rotational bearing 20 disposed between the central portion 14 and the distal portion 12, which allows the distal portion 12 to rotate independently of the central portion 14. The distal portion 12 may have a flexible rib-like construction with multiple individual ribs 22 connected together to create an elongate tube with a lumen 15. These ribs 22 may be made of a variety of materials, such as polycarbonate, nylon, polyethylene, polypropylene, and polyoxymethylene. The accessory channels 16, 18 may travel through the ribs 22 to the distal end section 24 of the distal portion 12. The distal end section 24 may include a pivot arm 26 with first and second accessory lumens 28, 30 (shown in FIGS. 3 and 4). The distal ends of the accessory channels 16, 18 may be fixedly or movably disposed within respective accessory lumens 28, 30. The distal end section 24 may also include a side port 32 that provides access from the lumen 15 to a point external the endoscope system 10.

Figure 3:
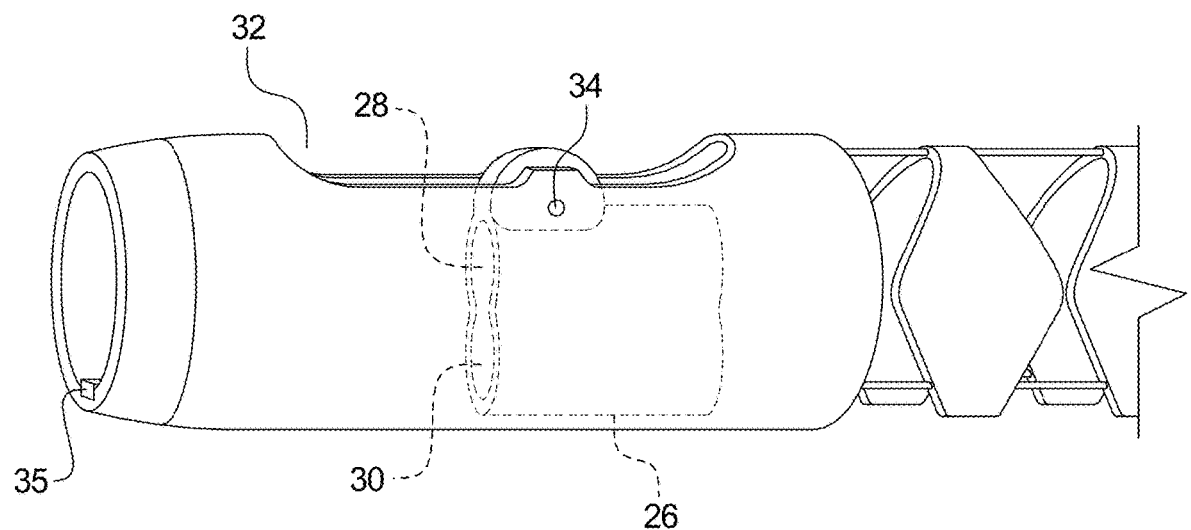
FIG. 3 is a detailed view of a pivot arm in a forward-facing configuration.
Figure 4:
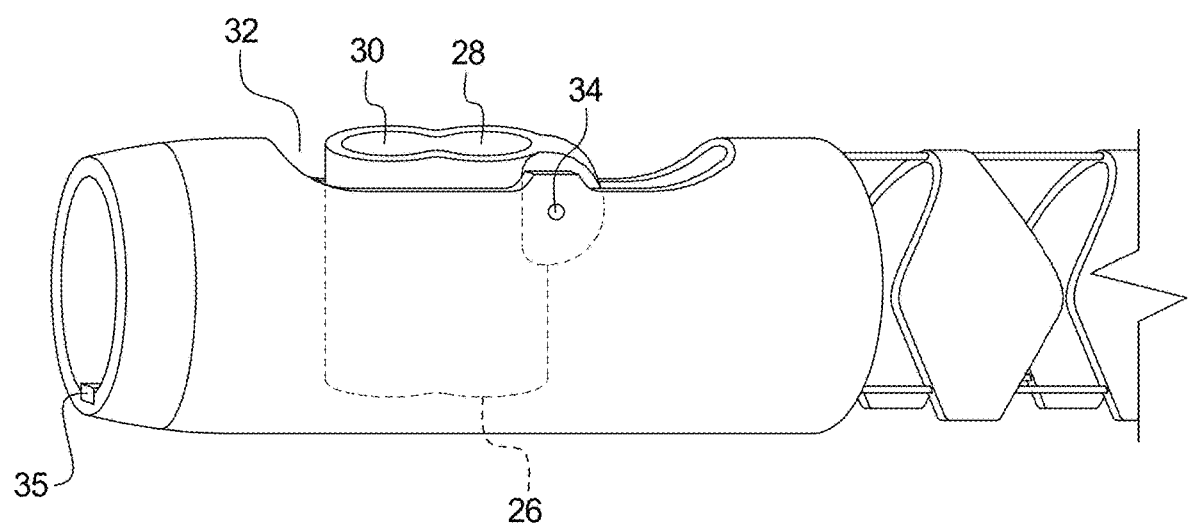
FIG. 4 is a detailed view of a pivot arm in a side-facing configuration.

The distal end section 24 of the distal portion 12 is shown in more detail in FIGS. 3 and 4. For clarity, the accessory channels 16, 18 are omitted from FIGS. 3 and 4. The pivot arm 26 may be connected to the distal end section 24 via a pin 34. The pin 34 may create a pivot point, around which the pivot arm 26 may rotate with respect to the distal end section 24 to the position shown in FIG. 4. The pivot arm 26 may be moved between a forward-viewing position as shown in FIG. 3 and a side-viewing position as shown in FIG. 4. A LED light 35 may be placed on the distal end section 24 to assist in navigation through a patient's GI tract. Alternatively, the LED light 35 may be placed at other locations on the distal end section 24, such as near the side port 32. Also, multiple LED lights 35 may be used at various locations on the system 10.

Figure 5:
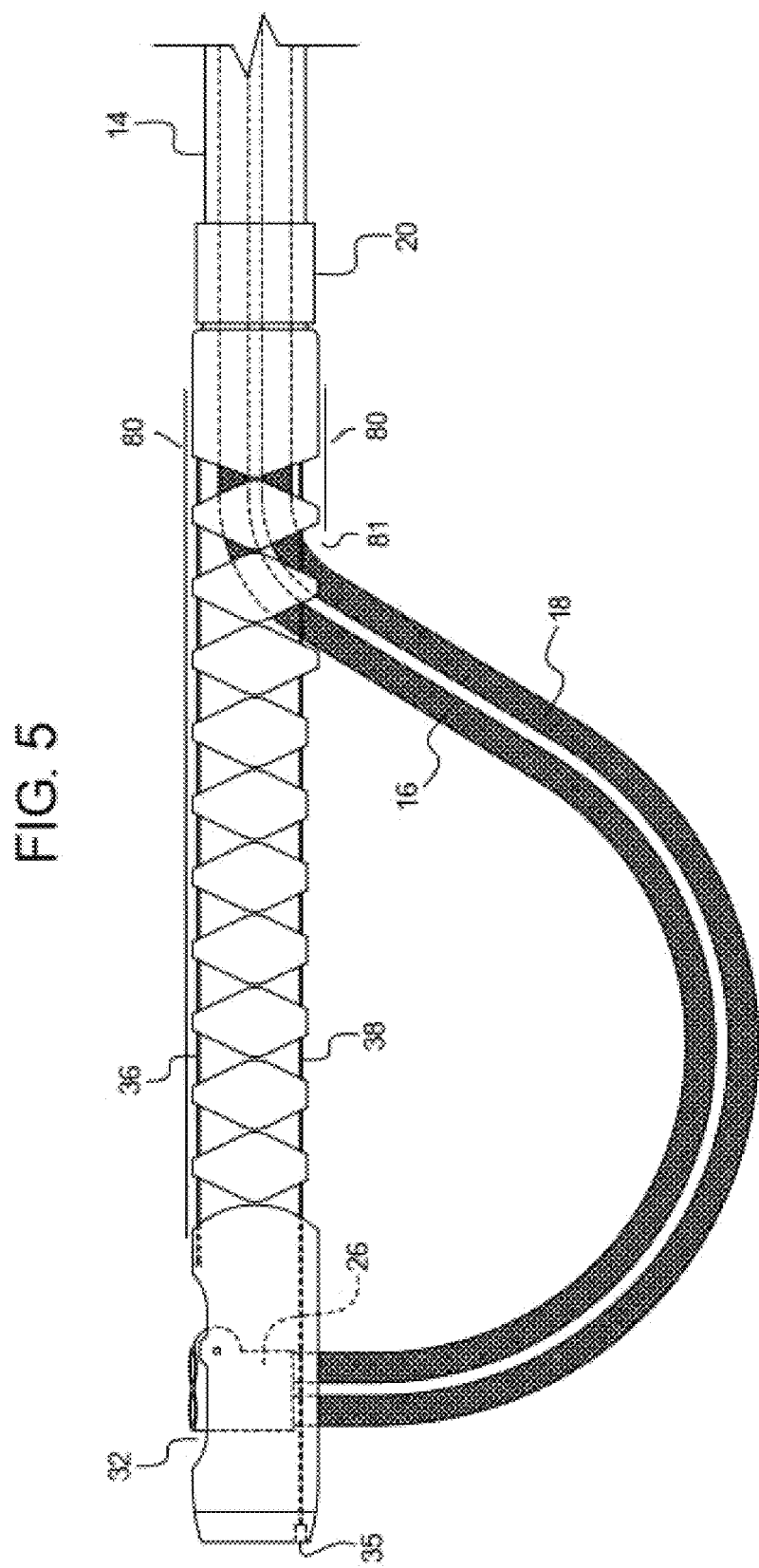
FIG. 5 is a detailed view of the distal portion of an endoscope system in a side-facing configuration.

As shown in FIGS. 2 and 5, the distal ends of the accessory channels 16, 18 may be secured to the pivot arm 26. Therefore, the accessory channels 16, 18 may rotate with the pivot arm 26 when moving the pivot arm 26 between the side-viewing and forward-viewing configurations. FIG. 2 shows the accessory channels 16, 18 in the forward-viewing configuration, while FIG. 5 shows the accessory channels 16, 18 in the side-viewing configuration. As can be seen in FIG. 5, when in the side-viewing configuration and due to the rotation of the pivot arm 26, distal portions of the accessory channels 16, 18 are bent outside of the confines of the ribs 22 and then curve back towards and into the pivot arm 26. Thus, in the forward-viewing configuration, the angle of curvature or bending radius of the distal portion 12 is the same as the angle of curvature of the accessory channels 16, 18 such that the accessory channels 16, 18 and the distal portion 12 of the scope system 10 are substantially parallel; but in the side-viewing configuration, the angle of curvature or bending radius of the accessory channels 16, 18 is greater than the angle of curvature of the distal portion 12 such that distal portions of the accessory channels 16, 18 extend outside the lumen 15 of the distal portion 12. To facilitate movement between the two configurations, the ribs 22 may have a U or V-shaped design with an open section that allows the accessory channels 16, 18 to move freely in and out of the ribs 22 (best shown in FIG. 7).

To move the pivot arm 26 from the forward-viewing position to the side-viewing position, the accessory channels 16, 18 may be pushed in a distal direction relative to proximal portion 13 and central portion 14, which applies a force through the accessory channels 16, 18 to the pivot arm 26. The resulting force causes the pivot arm 26 to rotate about the pivot point of the pin 34, thereby moving the accessory channels 16, 18 and pivot arm 26 into the side-viewing configuration. To move back to the forward-viewing configuration, a proximal force may be applied to the accessory channels 16, 18 relative to proximal portion 13 and central portion 14, thereby transferring the proximal force to the pivot arm 26. The proximal force then causes the pivot arm 26 to again rotate around the pivot point of the pin 34 in the opposite direction, thereby moving the accessory channels 16, 18 and the pivot arm 26 back to the forward-viewing configuration. To ensure that the accessory channels 16, 18 move in unison during these movements, the accessory channels 16, 18 may be secured together at any point along the length of the system 10, or even along the entire length. In one example, the accessory channels 16, 18 may be secured together using plastic tubing throughout the entire length of the central portion. In another example, the accessory channels 16, 18 may be secured together at the portions of the accessory channels 16, 18 that extend outside the constraints of the distal portion 12 when the system 10 is in the side-viewing configuration.

While this embodiment describes the use of a pivot arm 26 to assist in transferring the accessory channels 16, 18 between forward-viewing and side-viewing configurations, a variety of other methods and structures may be used. Further, rather than using a single pivot arm 26, multiple pivot arms may be used, or one for each accessory channel 16, 18. Therefore, each accessory channel 16, 18 may be moved between the forward-viewing and side-viewing configurations independently of each other. Further, the degree of rotation of the pivot arm 26 between the forward-viewing and side-viewing configuration may vary, potential ranging from 45 degrees to greater than 135 degrees.

Figure 6:
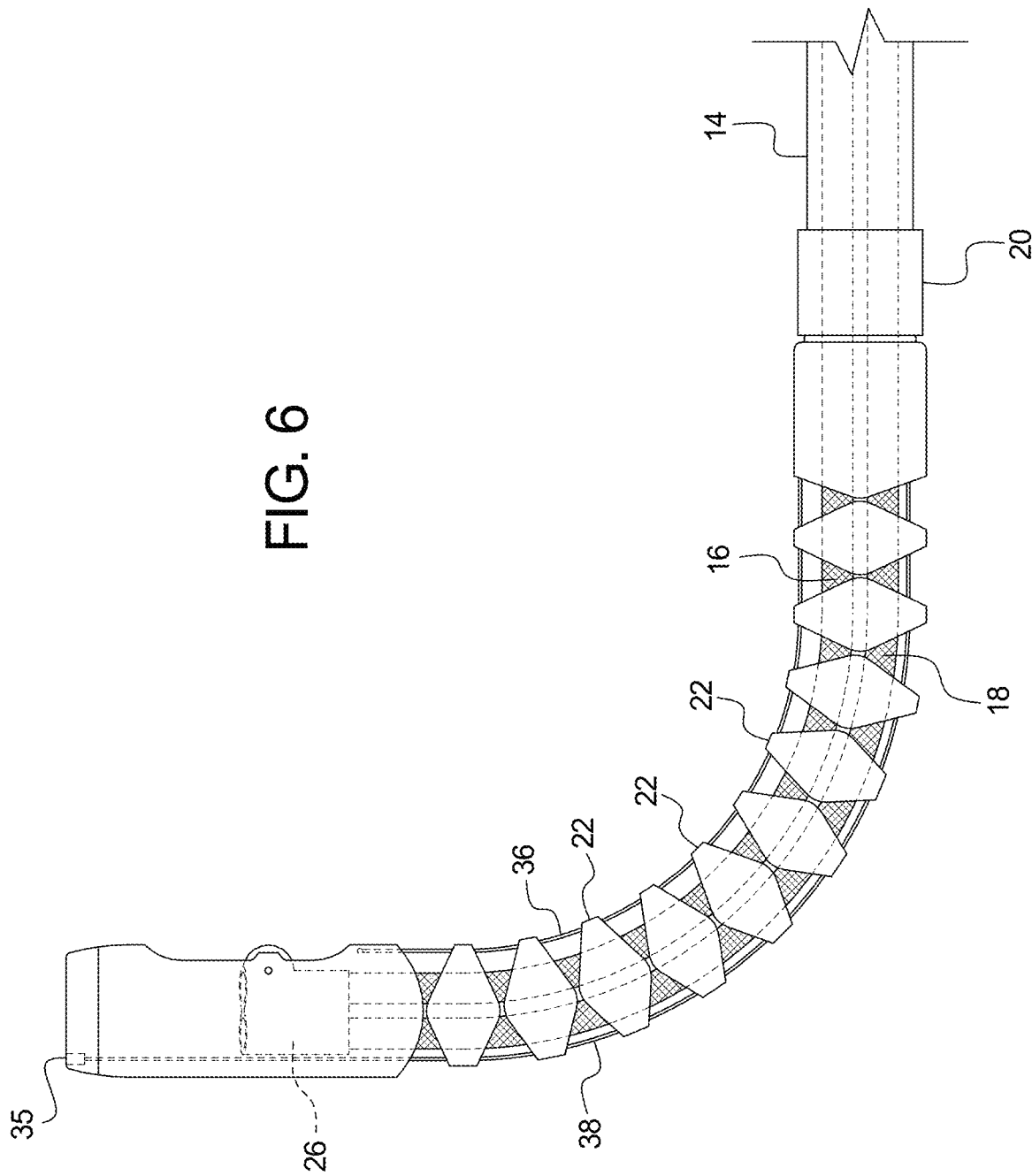
FIG. 6 is a detailed view of the distal portion of an endoscope system in a bent configuration.
Figure 7:
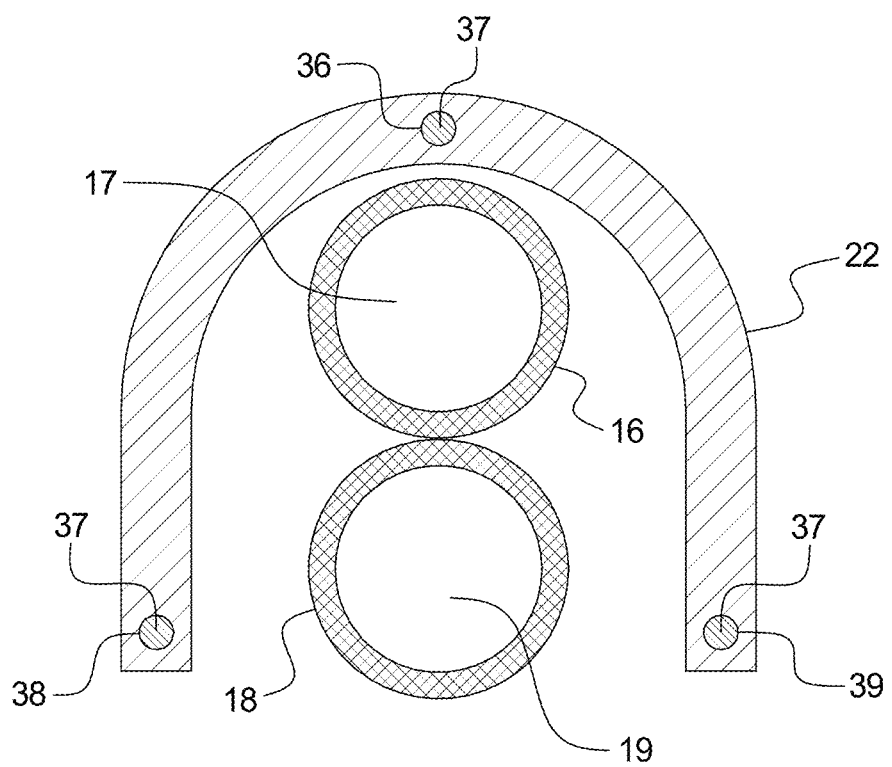
FIG. 7 is a cross-sectional view of a rib of an endoscope system.

In addition to the ability to switch between forward-viewing and side-viewing configurations, the distal portion 12 of the endoscope system 10 may also bend and rotate as desired. FIG. 2 shows the distal portion 12 in a straight configuration, while FIG. 6 shows the distal portion 12 in a bent configuration. The endoscope system 10 may include a first drive member 36, a second drive member 38, and a third drive member 39 (shown in FIG. 7). The second and third drive members 38, 39 may extend through the ribs 22 in the same plane of FIGS. 2 and 6, so only the second drive member 38 is representatively shown in those figures. FIG. 7 shows one potential orientation of the three drive members 36, 38, 39 in a cross-sectional view. The drive members 36, 38, 39 may be fixedly attached to the distal end section 24 and extend through, or outside of the lumen 15 to the handle portion 13. Alternatively, the drive members 36, 38, 39 may extend through dedicated low friction lumens or catheters along the length of the endoscope system 10 to the handle 13. The first drive member 36 may be fixed on a wall of the distal end section 24 while the second and third drive members 38, 39 may be fixed on an opposing wall of the distal end section 24 with respect to the first drive member 36. To move the distal portion 12 from the straight configuration shown in FIG. 2 to the bent configuration shown in FIG. 6, the first drive member 36 may be pulled in a proximal direction. This proximal movement of the first drive member 36 may result in a force being applied through the first drive member 36 and to the distal end section 24. This force may cause the flexible, ribbed body of the distal portion 12 to bend towards the configuration shown in FIG. 6. To move the distal portion 12 back to the straight configuration, the second and third drive members 38, 39 may be pulled in a proximal direction. Since the second and third drive members 38, 39 are connected to the opposite side of the distal end section 24, a force is applied through the second and third drive members 38, 39 and to the distal end section 24 that may move the distal portion 12 back towards the straight configuration.

The drive members 36, 38, 39 may also be used to secure the individual ribs 22 of the distal portion 12 together, as shown in the cross-sectional view of an individual rib 22 in FIG. 7. The drive members 36, 38, 39 may run through small holes 37 in each individual rib 22, and sufficient tension may be applied to the drive members 36, 38, 39, thereby securing the ribs 22 together along the drive members 36, 38, 39. Due to this design, the ribs 22 may be shaped to allow for minimal contact between the individual ribs 22. For example, the ribs 22 shown in this embodiment have a substantially U-shaped cross-section with an opening and two sides. Each side of the ribs 22 may be diamond shaped when viewing the system 10 from a side angle (as best seen in FIGS. 3-4). The diamond shape reduces the contact points between each rib, thus minimizing friction and allowing for easier bending of the distal portion 12 to the bent configuration and maximum flexibility. Optionally, the second or third drive members 38, 39 may also include built-in electrical wiring that allows the second or third drive members 38, 39 to function as a circuit for the LED light 35 as well. Further, while this embodiment only describes the use of three drive members 36, 38, 39 more or less drive members may be used as desired. Alternatively or in addition to the drive members 36, 38, 39, the ribs 22 may be connected together using a variety of other methods, such as with mechanical hinges, adhesives, and other well-known devices. Further, additional elongate members may extend through the ribs 22 similar to the drive members 36, 38, 39 to provide additional support to the distal portion 12.

Additionally, the ribs 22 may be covered by a protective sleeve 80 that may be made up of various biocompatible materials, such as an elastomeric material. The protective sleeve 80 may protect the ribs 22 while also preventing body tissue from accidentally being pinched between the individual ribs 22 when the distal portion 12 is moved between the bent configuration and the straight configuration. The protective sleeve 80 may also include a slot 81 that corresponds to the openings in the ribs 22 that allows the accessory channels 16, 18 to move outside of the protective sleeve 80 and between the forward-viewing configuration and the side-viewing configuration. The protective sleeve 80 may also help with torque transmission when moving the distal portion 12 between the bent and straight configurations. Some natural lag may occur when manipulating the drive members 36, 38, 39 that may cause part of the distal portion 12 to move first, while the rest of the distal portion lags behind, but eventually moves as well. The protective sleeve 80 may ensure that the entire distal portion 12 moves together and with minimal lag.

Figure 8:
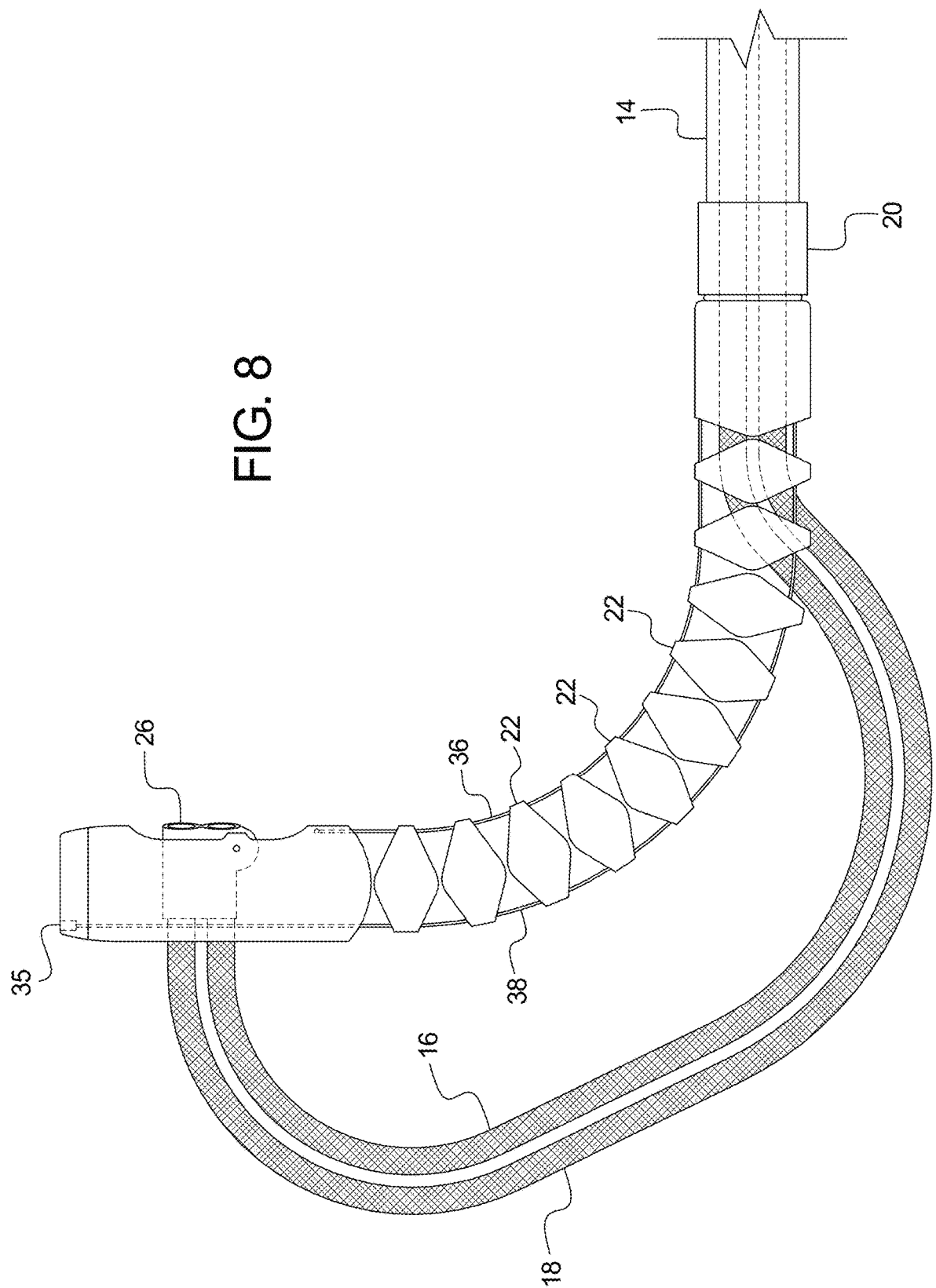
FIG. 8 is a detailed view of the distal portion of an endoscope system in a bent and side-facing configuration.

The endoscope system 10 may move between a bent configuration and a straight configuration while the endoscope system 10 is also in either the forward-facing or side-facing configurations. For example, FIG. 8 shows the endoscope system 10 in a bent and side-facing configuration. The endoscope system 10 can be manipulated and used in any combination of the above mentions configurations, and may be repeatedly movable between all configurations.

The accessory channels 16, 18 may be used to provide access for a variety of medical tools and accessories through the endoscope system 10 and into a patient's body. For example, a camera system may be inserted into one of the accessory channels 16 while a variety of tools such as forceps, sphincterotomes, wires, dilation balloons, extraction balloons, stents, needle knives, hemostasis clips, and any other catheter based tool may be inserted into the second accessory channel 18. The tools may be advanced past the distal ends of the accessory channels 16, 18 where they may be used to operate on a patient.

Figure 9:
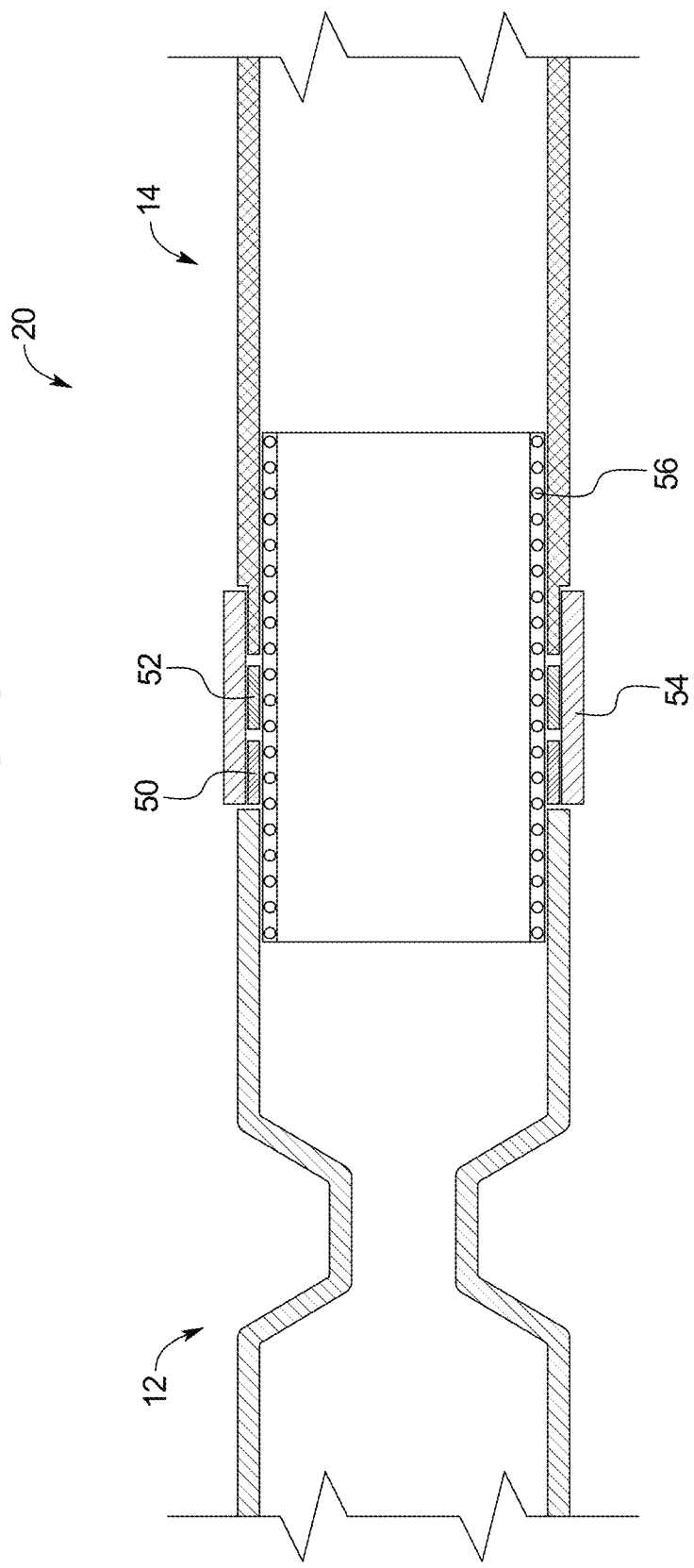
FIG. 9 is a detailed view of an axially rotatable bearing of an endoscope system.

FIG. 9 shows a cross-sectional view of the axially rotatable bearing 20 and its functionality. The axially rotatable bearing 20 may include a first ring 50 and a second ring 52. The axially rotatable bearing 20 may further include a first tube 54 and a second tube 56. The first tube 54 may be fixedly attached to the central portion 14 and the first ring 50. The second tube 56 may be fixedly attached to the distal portion 12 and the second ring 52. The first tube 54 and first ring 50 may be freely rotatable with respect to the second tube 56 and second ring 52, thereby making the distal portion 12 freely rotatable with respect to the central portion 14. Since the first ring 50 is indirectly secured to the central portion 14, but is located distal the second ring 52 which is indirectly secured to the distal portion 12, the distal portion 12 and central portion 14 may remain secured to each other while still remaining freely rotatable with respect to each other. The distal portion 12 may be freely rotated when the endoscope system 10 is in any one of the configurations described above, including forward-facing, side-facing, straight, and bent configurations. The accessory channels 16, 18 and the drive members 36, 38, 39 may pass freely through the lumen 15 of the bearing with causes no or minimal interference to the bearing 20. This is merely one potential design for the axially rotatable bearing 20, and various other designs that allow free rotation of the distal portion 12 with respect to the central portion 14 may be used.

Figure 10:
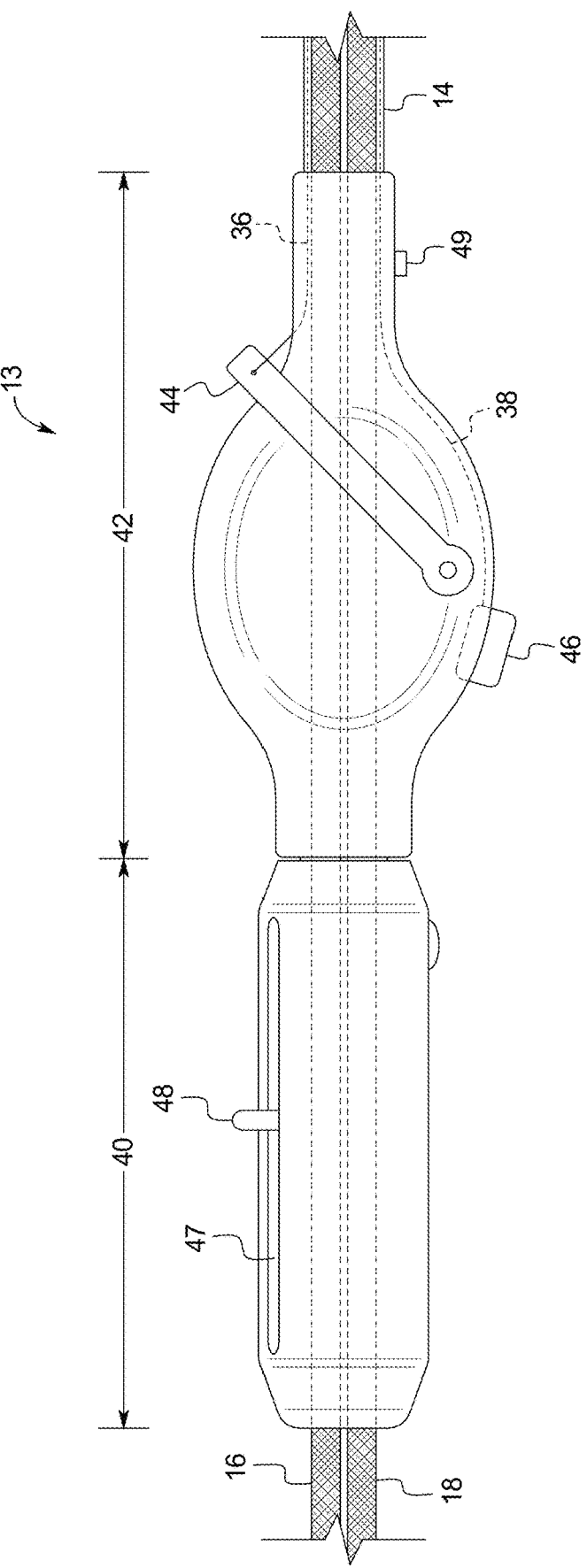
FIG. 10 is a detailed view of a handle of an endoscope system.

Now referring to FIG. 10, a detailed view of the handle portion 13 of the endoscope system 10 is shown. The handle 13 may include several controls used to manipulate the distal portion 12 of the endoscope system 10. The handle 13 may be include a first portion 40 and a second portion 42, where the first portion 40 is freely rotatable with respect to the second portion 42. The handle 13 may include an arm 44 that is connected to the first drive member 36, which is further connected to the distal end section 24. The arm 44 may be moved and/or pivoted in a proximal direction, which causes the first drive member 36 to be pulled in a proximal direction, thereby applying a proximal force to the distal end section 24 and causing the distal portion 12 to bend as shown in FIG. 6. The handle 13 may further include a first slider 46, which may be connected to the second and third drive member 38, 39, which is further connected to the distal end section 24. Similarly to the arm 44, the first slider 46 may be moved in a proximal direction which results in a proximal force being applied to the distal end section 24 through the second and third drive members 38, 39, thereby causing the distal portion 12 to bend back towards, and even past, the position shown in FIG. 2.

The handle 13 may further include a second slider 48, which may be slid along a slot 47 in a proximal and distal direction. The second slider 48 may be connected to the first and second accessory channels 16, 18, where proximal or distal movement of the second slider 48 causes corresponding movement of the first and second accessory channels 16, 18. Therefore, moving the second slider 48 in a distal direction causes the accessory channels 16, 18 to move in a distal direction, thereby causing the pivot arm 26 to rotate and move into the side-viewing configuration. Further, moving the second slider 48 in a proximal direction causes the pivot arm 26 to rotate back towards the forward-viewing configuration. Also, as discussed earlier, the first portion 40 may be rotated freely with respect to the second portion 42. Since the accessory channels 16, 18 are fixed to the second slider 48, rotation of the first portion 40 may cause corresponding rotation of the accessory channels 16, 18. Since, the accessory channels 16, 18 are also fixed at their distal ends to the pivot arm 26, which is in turn fixed to the rest of the distal portion 12 of the system 10, rotation of the first portion may cause corresponding rotation of the entire distal portion 12. Further, since the axially rotatable bearing 20 as shown in FIG. 9 is disposed between the distal portion 12 and central portion 14, the distal portion 12 may rotate in response to rotation of the first portion 40 of the handle 13 without the rest of the system 10 rotating. Additionally, a knob 49 may be used to control the brightness or power of the LED light 35, which is wired to the knob 49 at least partially through the second and/or third drive members 38, 39.

The handle 13 is merely one potential embodiment of the handle portion 13, and any other handle design capable of controlling the endoscope system 10 may be used, including variations on the arms or sliders that control various features of the system 10. For example, the handle 13 and various controls such as the arm 44 and sliders 46, 48 may include locking elements that lock the system in the various aforementioned configurations. In one example, the handle 13 may include frictional locks, where the various arms and sliders may be maintained in their current position with a frictional force. However, the application of an external force may still move the controls as desired. In another alternative handle 13 design, the arm 44 may have a pivot point in the center of the handle, with one end of the arm 44 connected to the first drive member 36 and the other end of the arm 44 connected to the second and third drive members 38, 39, thus allowing the arm 44 to control both directions of bending motion for the distal portion 12.

Figure 11:
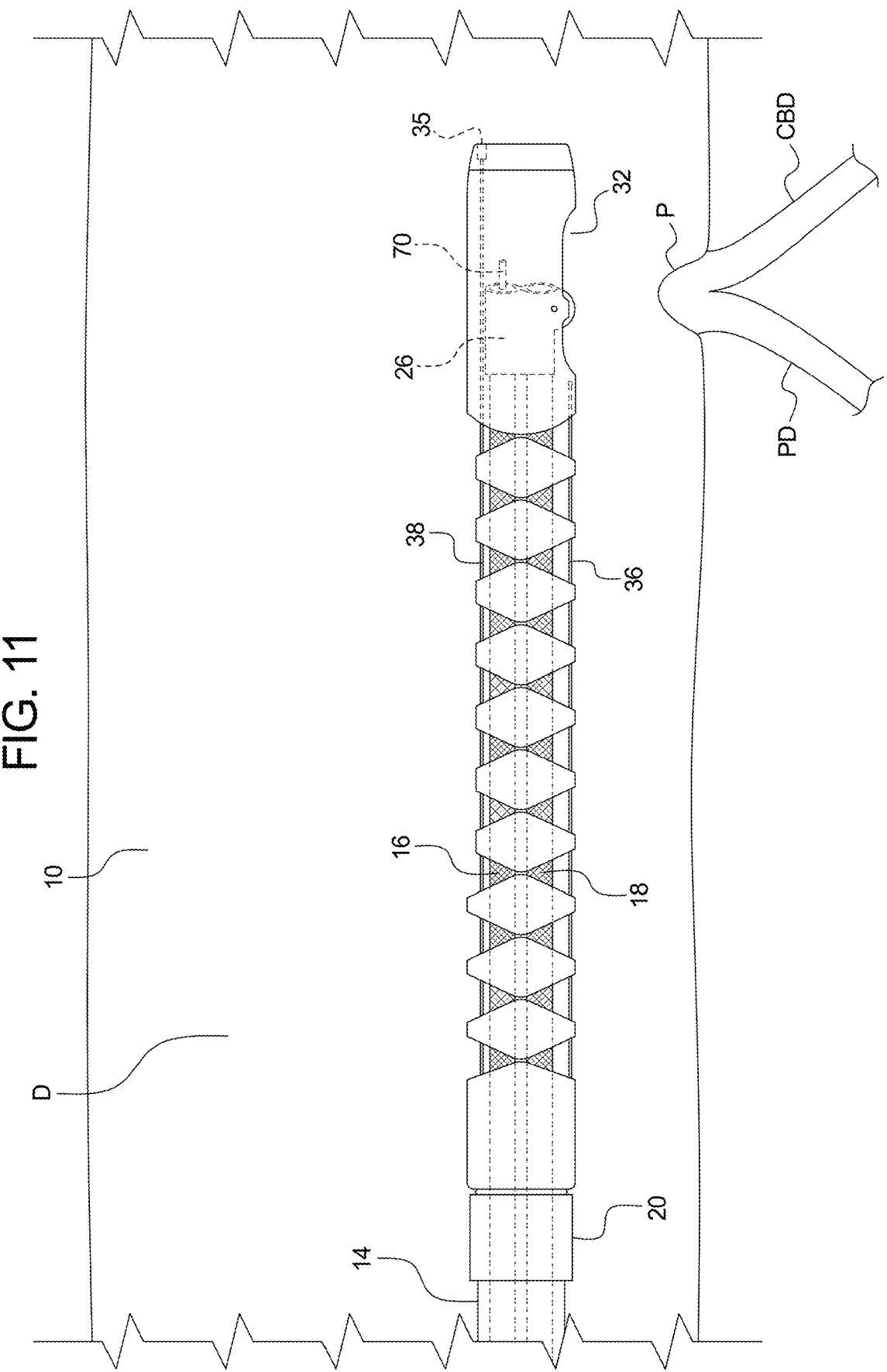
FIG. 11 is a pictorial representation of an endoscope system in use.

The endoscope system 10 described herein may be used for a variety of medical procedures. However, one such procedure, an endoscopic retrograde cholangiopancreatography (ERCP), is now described with reference to FIGS. 11-13. The endoscope system 10 may be inserted into a patient's mouth and through the gastrointestinal tract. It may be preferable to insert the endoscope system 10 in the forward-facing position, which provides a lower profile than the side-facing position, thus making advancement through the gastrointestinal tract easier. Further, a camera system 70 may be inserted into one of the accessory channels 16 to assist the physician in guiding the endoscope system 10 through the patient's gastrointestinal tract. The camera system 70 may be integral with the accessory channel 16, or it may be advanceable past the distal end of the accessory channel 16. Further, the camera system 70 may include a light source independent of the rest of the system 10. The camera system 70 may be positioned in the accessory channel 16 such that the distal end of the camera system extends into or just past the pivot arm 26, thus providing a clear view of the distal end of the endoscope system 10 as it is advanced. The endoscope system 10 may be advanced past the stomach and into the duodenum D until the distal end section 24 is disposed near the papilla of Vater P as shown in FIG. 11.

Figure 12:
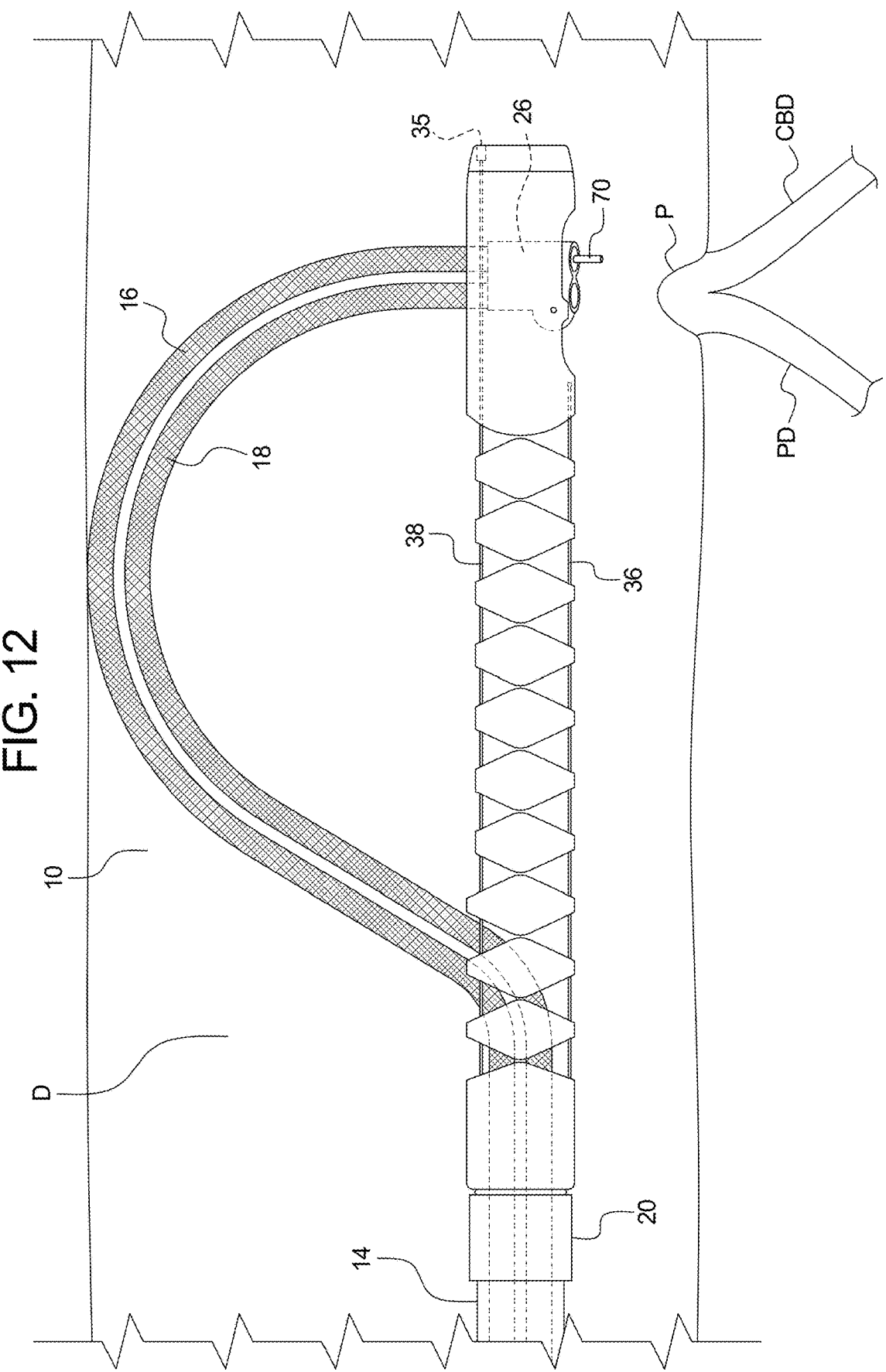
FIG. 12 is another pictorial representation of an endoscope system in use.

Once the distal end section 24 is disposed near the papilla of Vater P, the distal portion 12 may be bent or straightened using the arm 44 and first slider 46 of the handle 13 until the distal end section 24 is substantially perpendicular to the papilla of Vater P. The distal portion 12 may be further rotated by the first portion 40 of the handle 13 so that the side port 32 is aimed towards the papilla of Vater P. The accessory channels 16, 18 may next be moved from the forward-facing configuration to the side-facing configuration by moving the second slider 48 of the handle 13 in a distal direction until the pivot arm 26 rotates to the side-facing configuration. The distal portion 12 may be further manipulated by the controls of the handle 13 until the distal end section 24 is properly positioned with relation to the papilla of Vater P as shown in FIG. 12. In this position, the accessory channels 16, 18 have a direct and straight line of access to the papilla of Vater P. FIG. 12 further shows at least one of the accessory channels 16, 18 contacting the wall of the duodenum D opposite the papilla of Vater P. This contact helps push the entire endoscope system 10 closer to the papilla of Vater P and provides an anchor point to help secure the endoscope system 10 within the duodenum or other target portion of the anatomy.

Figure 13:
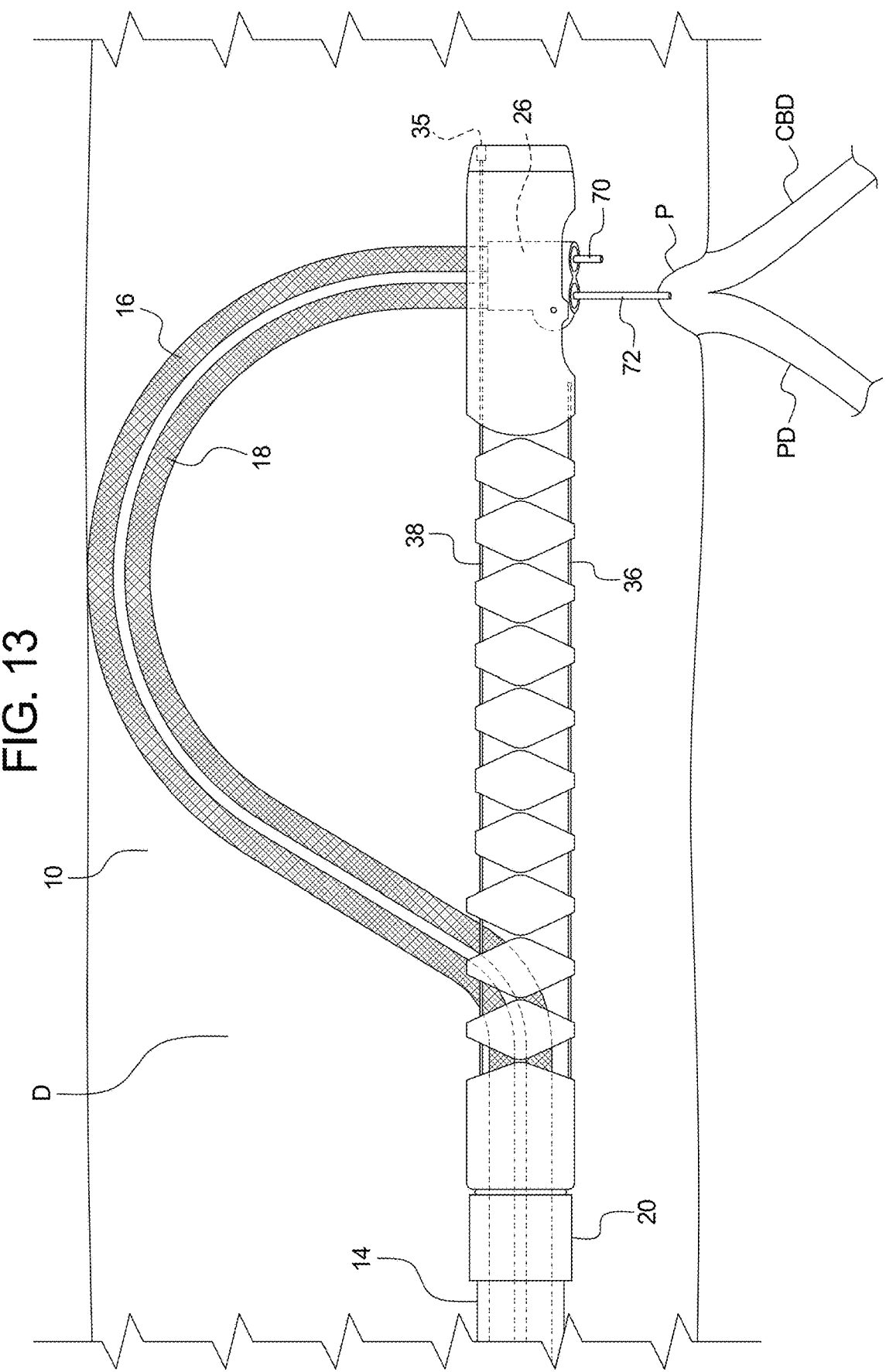
FIG. 13 is another pictorial representation of an endoscope system in use.

At this point, a variety of tools may be used to access the pancreatic duct D or the common bile duct C through the papilla of Vater P. If a camera system 70 was used previously, it may optionally be removed to allow for additional tools to be used. The gradual, curved path of the accessory channels 16, 18 may reduce friction between the accessory channels 16, 18 and tools, thus reducing the amount of force required for the physician to advance the tools towards the papilla of Vater P. For example, the sphincter of Oddi, a strong muscle found within the papilla of Vater P, may need to be dilated or cut to allow access into the common bile duct CBD or pancreatic duct PD. Therefore, a sphincterotome 72, a long tool with a thin wire capable of cutting through the sphincter of Oddi, may be advanced through the accessory channel 18 and towards the papilla P as shown in FIG. 13. The sphincterotome 72 may then be used to cut into the sphincter of Oddi, therefore creating an access point into the common bile duct CBD and pancreatic duct PD. Physicians often have difficulty properly positioning the sphincterotome 72 or other dilation tools towards the sphincter and providing sufficient force to the sphincter. The accessory channels 16, 18 contacting the opposite wall of the duodenum D provides an anchor point that may allow the physician to apply a sufficient amount of force to the sphincterotome 72 or other tools without fear of losing positioning of the endoscope system 10. Once an access point has been created, a variety of tools, including the camera system 70, radiopaque dye injector, kidney stone retriever, etc. may be advanced through either of the accessory channels 16, 18 and into the common bile duct CBD or pancreatic duct PD.

Following completion of the procedure, the various tools used may be withdrawn and the endoscope system 10 may be moved to the straight configuration and the forward-viewing configuration, thus permitting the physician to remove the endoscope system 10 from the patient's body in substantially the same was as it was inserted.

Figure 14:
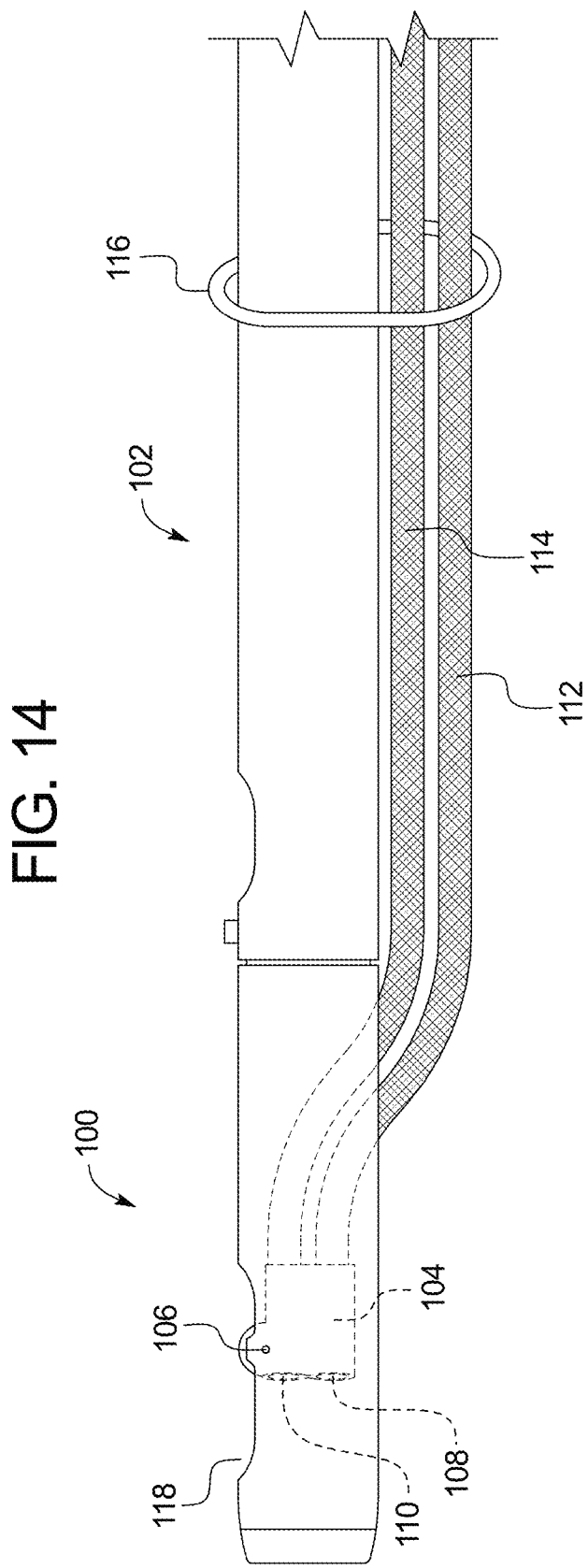
FIG. 14 is a drawing of an endoscope cap in a forward-viewing configuration.

In a second embodiment shown in FIG. 14, a scope cap 100 may be attachable to a standard duodenoscope or endoscope. The scope cap 100 has many of the features of the aforementioned embodiments. The scope cap 100 may be removably or fixedly attached to a duodenoscope 102 using a variety of methods, including a friction fit, elastic belt, and adhesives. Alternatively, the scope cap 100 may be attached to an endoscope, cholangioscope, or any other similar devices. The endoscope cap 100 may include a pivot arm 104. The pivot arm 104 may be similar to the pivot arm described in previous embodiments, with a pin 106 creating a pivot point around which the pivot arm 104 may rotate with respect to the rest of the scope cap 100. The pivot arm 104 may further include a first pivot lumen 108 and a second pivot lumen 110. A first accessory channel 112 and a second accessory channel 114, each with respective lumens, may be connected to the respective pivot lumens 108, 110. The accessory channels 112, 114 may run from the pivot arm 104, along the outside of the duodenoscope 102, and to or near the proximal end of the duodenoscope 102. Multiple clips 116 (only one shown in FIG. 14) may be used to secure the accessory channels 112, 114 to the duodenoscope 102. The clips 116 may be spaced apart the entire length of the duodenoscope 102, thus ensuring that the accessory channels 112, 114 do not separate significantly from the duodenoscope 102. It may be ideal for the clips 116 to still permit longitudinal movement of the accessory channels 112, 114 along the length of the duodenoscope 102, while restricting or limiting other movement. For example, clips 116 may be fixedly connected to accessory channels 112, 114, and slidably connected to the scope 102. While clips 116 are used in this example, a variety of other attachment methods may be used such as loops or rings that may be slide along the length of the duodenoscope 102 to a desired location.

Figure 15:
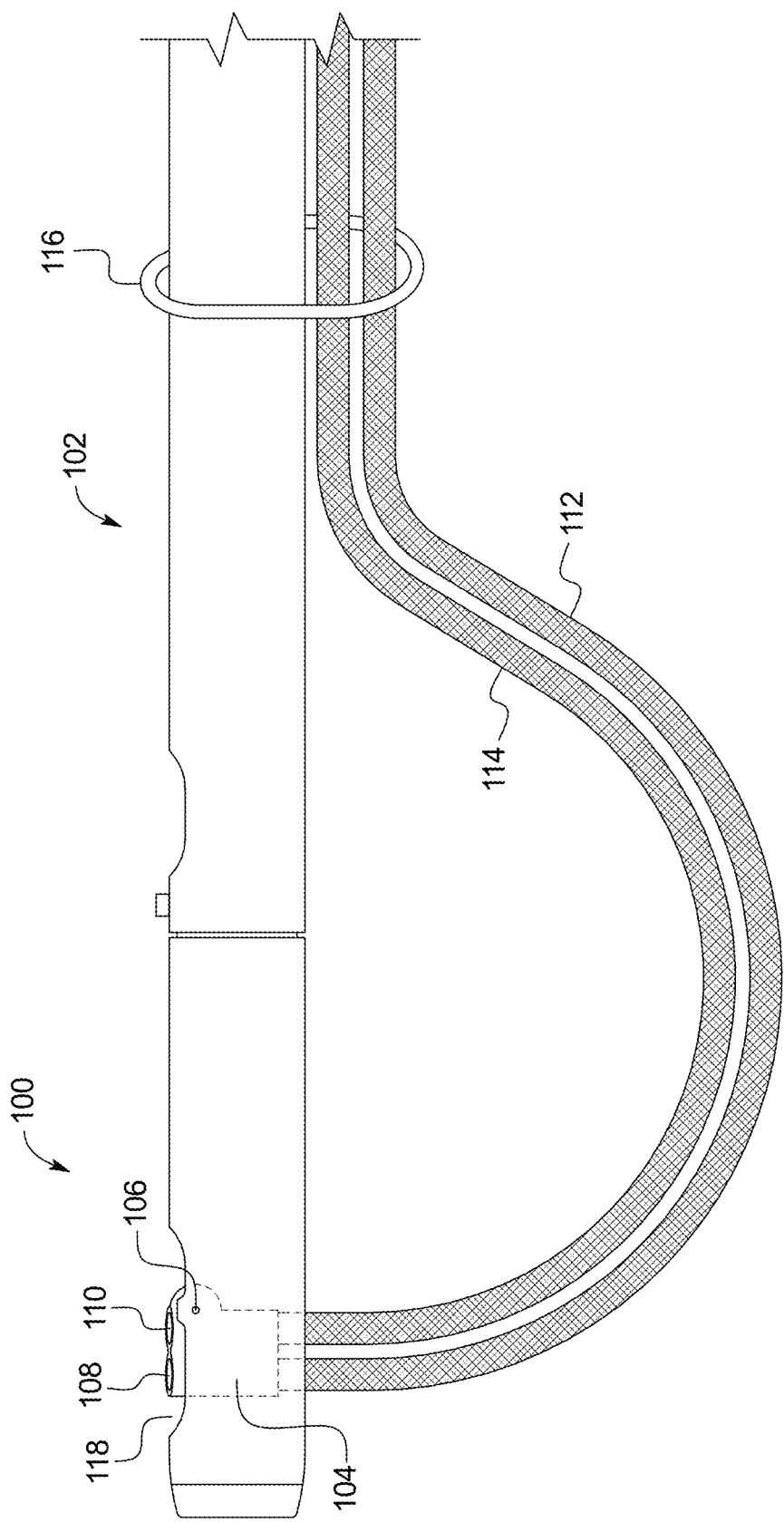
FIG. 15 is a drawing of an endoscope cap in a side-viewing configuration.

The scope cap 100 may move between a forward-viewing configuration as shown in FIG. 14 and a side-viewing configuration as shown in FIG. 15. To move the scope cap 100 from the forward-viewing configuration to the side-viewing configuration, the accessory channels 112, 114 may be advanced in a distal direction with respect to the duodenoscope 102 and scope cap 100. This movement results in a force being applied to the pivot arm 104, thereby causing the pivot arm 104 to rotate about the pivot point 106 and thereby move the scope cap 100 into the side-viewing configuration as shown in FIG. 15. In the side-viewing configuration, the pivot arm 104 may be rotated about 90 degrees in comparison to the forward-viewing configuration, while the accessory channels 112, 114 may bend away from the duodenoscope 102 and then bend back towards the scope cap 100 substantially perpendicular to the length of the duodenoscope 102. Alternatively, the pivot arm 104 may be rotated at a variety of angles, potentially ranging anywhere from 45 degrees to greater than 135 degrees. To facilitate this bend or arch, it may be ideal to provide a sufficient amount of space between the most distal clip 116 and the scope cap 100, thus permitting the accessory channels 112, 114 to bend away from the duodenoscope between the most distal clip 116 and scope cap 100 with minimal restriction. When in the side-viewing configuration, an opening 118 in the scope cap 100 may permit tools or accessories passed through the accessory channels 112, 114 to be advanced past the scope cap 100.

In use, the scope cap 100 may be used in an ERCP procedure in a manner similar to the embodiments described above. The scope cap 100 may be preinstalled to a duodenoscope 102 or other scope, or a physician or other operator may attach the scope cap 100 and accessory channels 112, 114 to any standard, existing scope. The scope cap 100 may be attached to the distal end of the duodenoscope 102, while the clips 116 may be used to secure the accessory channels 112, 114 to the outside of the duodenoscope 102. The duodenoscope 102, along with the scope cap 100 and accessory channels 112, 114, may then be inserted into a patient's mouth in the forward-viewing configuration and advanced through the gastrointestinal tract until the scope cap 100 is positioned near the papilla of Vater. The accessory channels 112, 114 may then be advanced distally so as to cause the pivot arm 104 to rotate about the pivot point 106 and to the side-viewing configuration. Various accessories or tools may then be advanced through the accessory channels 112, 114 and used as desired.

The endoscope system 10 and scope cap 100, or any portions thereof, may be designed to be disposable, thus reducing the risk of bacterial infection due to incomplete cleaning between uses.

While the embodiments described herein are shown in reference to the endoscopy field and endoscopic retrograde cholangiopancreatography procedures, the embodiments may be used in a variety of other medical procedures including endoscopic submucosal dissection and any other endoscopic procedure that would benefit by having multiple instruments at a time and/or the ability to see things from both the forward-viewing and side-viewing perspectives.

The description of the disclosure is merely exemplary in nature and, thus, variations that do not depart from the substance of the disclosure are intended to be within the scope of the disclosure. Such variations are not to be regarded as a departure from the spirit and scope of the disclosure.

We claim:

1. A scope system, comprising:
an elongate tube comprising a lumen extending therethrough from within a handle through a proximal portion of the elongate tube and through a distal portion of the elongate tube; and
at least one accessory channel comprising a tubular structure comprising an accessory lumen extending longitudinally through the tubular structure, where the at least one accessory channel is movably disposed at least partially within the lumen of the elongate tube, the at least one accessory channel comprising a distal section of the accessory channel, where the at least one accessory channel being movable between a forward-viewing configuration and a side-viewing configuration, wherein—in the forward-viewing configuration—the distal section of the at least one accessory channel is substantially parallel to the distal portion of the elongate tube;
where the distal portion of the elongate tube comprises a plurality of individual ribs covered by a protective sleeve configured to protect the ribs and to prevent material adjacent the ribs from being pinched between the individual ribs when the distal portion of the elongate tube is moved between the forward-viewing configuration and the side-viewing configuration; and
wherein—in the side-viewing configuration—the distal section of the at least one accessory channel extends out through an opening of at least one of the ribs and is arced outside the elongate tube.

2. The scope system of claim 1, wherein:
in the side-viewing configuration, an intermediate portion of the distal section of the at least one accessory channel is arced outside the lumen of the distal portion of the elongate tube.

3. The scope system of claim 1, wherein:
in the forward-viewing configuration, the distal section of the at least one accessory channel is disposed within the lumen of the distal portion of the elongate tube.

4. The scope system of claim 1, wherein:
movement of a proximal portion of the at least one accessory channel in a distal direction relative to the elongate tube moves the at least one accessory channel from the forward-viewing configuration to the side-viewing configuration.

5. The scope system of claim 1, wherein:
movement of a proximal portion of the at least one accessory channel in a proximal direction relative to the elongate tube moves the at least one accessory channel from the side-viewing configuration to the forward-viewing configuration.

6. The scope system of claim 1, wherein:
a distal-most portion of the distal section of the accessory channel is rotatably coupled to the distal portion of the elongate tube.

7. The scope system of claim 1, wherein:
the distal portion comprises a pivot point, wherein during movement of the at least one accessory channel between the forward-viewing configuration and the side-viewing configuration, the at least one accessory channel rotates about a pivot point.

8. The scope system of claim 1, wherein:
in the side-viewing configuration, the distal section of the at least one accessory channel that extends out through the opening of the at least one of the ribs is curved with a bending radius that is different than a bending radius of the distal portion of the elongate tube.

9. The scope system of claim 1, wherein the protective sleeve includes a slot that corresponds to the opening of at least one of the ribs in a manner that allows the at least one accessory channel to move through the slot to outside of the protective sleeve.

10. The scope system of claim 1, wherein the protective sleeve includes an elastomeric material and is configured to transmit torque between the plurality of individual ribs.

11. The scope system of claim 1, wherein:
a camera system is fixedly disposed relative to the accessory lumen.

12. The scope system of claim 1, further comprising:
first and second drive mechanisms connected to the distal portion of the elongate tube and extending proximally along the elongate tube;
wherein proximal movement of the first drive mechanism bends the distal portion of the elongate tube in a first direction, and proximal movement of the second drive mechanism bends the distal portion of the elongate tube in a second direction.

13. The scope system of claim 12, wherein:
the second direction is opposite the first direction.

14. The scope system of claim 12, wherein:
the distal portion of the elongate tube comprises a plurality of individual ribs, the first and second drive mechanisms connecting the plurality of individual ribs together.

15. The scope system of claim 12, further comprising:
one or more lights connected to the distal portion, wherein one of the first and second drive mechanisms further comprises an electrical wiring between the light and a power source.

16. The scope system of claim 12, further comprising:
a third drive mechanism connected to the distal portion of the elongate tube and extending proximally along the elongate tube;
wherein proximal movement of the third drive mechanism bends the distal portion of the elongate tube in a third direction.

17. The scope system of claim 1, wherein:
the at least one accessory channel comprises a first accessory channel and a second accessory channel, wherein the first accessory channel is movable between the forward-viewing configuration and the side-viewing configuration independent from the second accessory channel.

18. The scope system of claim 1, wherein:
the at least one accessory channel comprises a first accessory channel and a second accessory channel; and
the accessory lumen comprises a first accessory lumen and a second accessory lumen, the first accessory lumen extending through the first accessory channel and the second accessory lumen extending through the second accessory channel, wherein a camera system is at least partially and removably disposed within the first accessory lumen.

19. A scope system, comprising:
an elongate tube comprising a lumen extending from within a handle with controls directly through a proximal portion and a distal portion of the elongate tube including a protective sleeve; and
at least one accessory channel comprising a tubular structure comprising an accessory lumen extending therethrough, the at least one accessory channel movably disposed from within the handle and through the proximal portion of the elongate tube and at least partially within the lumen of the elongate tube, the at least one accessory channel comprising a distal section, the at least one accessory channel further comprising a forward-viewing configuration and a side-viewing configuration;
wherein in the forward-viewing configuration, the distal section of the at least one accessory channel is disposed within the lumen of the distal portion of the elongate tube, the at least one accessory channel coupled to the distal portion via a pivot point at a distal end section of the elongate tube;
wherein in the side-viewing configuration, a portion of the distal section of the at least one accessory channel is arced away from and disposed external to the lumen of the distal portion of the elongate tube and outside of the protective sleeve of the distal portion of the elongate tube;
wherein a camera system is at least partially disposed within the distal section of the accessory channel, wherein, in the side-viewing configuration, a portion of the at least one accessory channel is arced outside of the elongate tube, the arced portion disposed between the pivot point at the distal end section of the elongate tube and a proximal end of the elongate tube.

20. A scope system, comprising:
an elongate tube comprising a lumen extending therethrough from within a handle through a proximal portion of the elongate tube and through a distal portion of the elongate tube; and
at least one accessory channel comprising a tubular structure comprising an accessory lumen extending longitudinally through the tubular structure, where the at least one accessory channel is movably disposed at least partially within the lumen of the elongate tube, the at least one accessory channel comprising a distal section of the accessory channel, where the at least one accessory channel being movable between a forward-viewing configuration and a side-viewing configuration, wherein—in the forward-viewing configuration—the distal section of the at least one accessory channel is substantially parallel to the distal portion of the elongate tube;
where the distal portion of the elongate tube comprises a plurality of individual ribs; and
wherein—in the side-viewing configuration—the distal section of the at least one accessory channel extends out through an opening of at least one of the ribs and is arced outside the elongate tube.

* * * * *